(12) United States Patent
Buijs et al.

(10) Patent No.: US 7,460,232 B2
(45) Date of Patent: Dec. 2, 2008

(54) ON-LINE OPTICAL ANALYSIS OF A SUBSTANCE THROUGH A CONDUIT SECTION OF A PROCESS LINE

(75) Inventors: Henry Buijs, Sillery (CA); Paul Chabot, Sainte-Foy (CA); Sylvain Dion, Sainte-Brigitte de Laval (CA); Benoit Turcotte, Neufchatel (CA)

(73) Assignee: ABB Bomem Inc., Quebec, Quebec (CA)

( * ) Notice: Subject to any disclaimer, the term of this patent is extended or adjusted under 35 U.S.C. 154(b) by 0 days.

(21) Appl. No.: 10/825,139

(22) Filed: Apr. 16, 2004

(65) Prior Publication Data

US 2004/0233453 A1 Nov. 25, 2004

(51) Int. Cl.
*G01N 21/85* (2006.01)
(52) U.S. Cl. .................................................. 356/410
(58) Field of Classification Search .................. 356/39, 356/40, 436, 440, 246
See application file for complete search history.

(56) References Cited

U.S. PATENT DOCUMENTS

| | | | | |
|---|---|---|---|---|
| 3,527,542 A * | 9/1970 | Penhasi et al. | ............... | 356/244 |
| 3,864,044 A * | 2/1975 | Lyshkow | ..................... | 356/436 |
| 3,899,688 A * | 8/1975 | Perieres | ...................... | 356/442 |
| 4,227,814 A * | 10/1980 | Soodak et al. | ................. | 356/39 |
| 4,312,341 A * | 1/1982 | Zissimopoulos et al. | ...... | 356/40 |
| 4,647,210 A * | 3/1987 | Morris et al. | ................ | 356/410 |
| 5,665,975 A * | 9/1997 | Kedar | .......................... | 356/436 |
| 6,144,444 A * | 11/2000 | Haworth et al. | ................ | 356/39 |
| 6,290,912 B1 * | 9/2001 | Doms | .......................... | 356/436 |
| 6,510,330 B1 * | 1/2003 | Enejder | ....................... | 356/39 |
| 6,687,004 B1 * | 2/2004 | Shana et al. | ................. | 356/436 |

* cited by examiner

*Primary Examiner*—Gregory J Toatley, Jr.
*Assistant Examiner*—Juan D Valentin
(74) *Attorney, Agent, or Firm*—Ogilvy Renault LLP

(57) ABSTRACT

A conduit-mounted light-transmitting device (10) for allowing optical analysis of a substance through a process line conduit (14) made of a light-transmitting material. The device (10) comprises a clip (24) adapted to be detachably secured about the conduit section. The clip (24) defines an optical path intersecting the conduit section when the clip (24) is mounted thereon.

16 Claims, 4 Drawing Sheets

ON-LINE OPTICAL ANALYSIS OF A SUBSTANCE THROUGH A CONDUIT SECTION OF A PROCESS LINE

BACKGROUND OF THE INVENTION

1. Field of the Invention

The present invention generally relates to spectroscopy and, more particularly, to a non-intrusive device for allowing spectrum analysis of a substance through a conduit section of a process line of a given processing plant.

2. Description of the Prior Art

It is known to carry out spectroscopy for monitoring the chemical composition and physical properties of various solutions used in processing plants, such as chemical, pharmaceutical, petroleum, semiconductors and food product processing industries. Typically, such a spectrum analysis is performed by extracting a sample of the substance to be analyzed from the process line of the processing plant and carrying out a spectrometric analysis of the collected sample by passing near to far infrared radiation therethrough.

Instead of the above-mentioned method, it would be preferable to perform the test on-line directly through a conduit section of the process line, and if the process line includes a conduit section made of a light-transmitting material directly through this existing conduit section, to avoid process line modifications.

SUMMARY OF THE INVENTION

It is therefore an aim of the present invention to provide a light-transmitting device adapted to be mounted on a processing line externally of a conduit section thereof for allowing spectrum analysis of a substance circulated through the conduit section.

It is also an aim of the present invention to provide for on-line analysis of a substance without having to extract a sample of the substance from the process line through which the substance is circulated.

It is a further aim of the present invention to provide a light-transmitting device for allowing spectrum analysis of a substance circulated through a process line without having to modify the process line when the latter includes a conduit section made of a light-transmitting material.

Therefore, in accordance with the present invention, there is provided a non-intrusive device for allowing spectrum analysis of a confined process stream through a light-transmitting conduit section of a process line, comprising a clip adapted to be externally mounted on the light-transmitting conduit section, said clip being at least partly made of a light-transmitting material and connectable to a source of light to direct a beam of light transversally through the conduit section.

The expression spectrum analysis is herein intended to mean the investigation of substances or bodies by means of their electromagnetic spectra, specifically chemical composition and physical properties analysis thereof.

The expression light is herein intended to mean all wavelengths included in the electromagnetic spectrum, including the ultraviolet, visible and infrared portions of the electromagnetic spectrum.

In accordance with a further general aspect of the present invention, there is provided a conduit-mounted light-transmitting device for allowing optical analysis of a substance through a conduit section of a process line, wherein said conduit section is made of a light-transmitting material, the conduit-mounted light-transmitting device comprising a clip adapted to be detachably secured about the conduit section, said clip defining an optical path intersecting the conduit section when said clip is secured thereabout.

BRIEF DESCRIPTION OF THE DRAWINGS

Having thus generally described the nature of the invention, reference will now be made to the accompanying drawings, showing by way of illustration a preferred embodiment thereof, and in which.

DESCRIPTION OF THE PREFERRED EMBODIMENTS

The present invention, as will be explained hereinafter, is generally directed to a light-transmitting device 10 adapted to be removably secured about a process line of a given processing plant to permit optical analysis of the composition and/or physical properties of a substance circulated through the process line. More specifically, the light-transmitting device 10 is adapted to be externally mounted on a conduit section of an existing process line to direct a light beam (visible, near infrared or infrared) from a remote light source (not shown), through the conduit section and then carry the light emerging from the illuminated substance through the conduit section to a light receiving sensor (not shown), such as a spectrophotometer. It is understood that the conduit section of the process line has to be made of optically transparent or translucent material such as polytetrafluoroethylene (PTFE), other fluorinated hydrocarbon polymers, and any other light/infrared transmitting material for allowing the light to pass transversally therethrough. For instance, the conduit section could be made of Teflon™, glass, polypropylene, polystyrene or other polymers.

As will be seen hereinafter the present invention advantageously allows on-line control and monitoring of a process stream without having to extract a product sample from the process line. There is thus no risk of contamination of the process stream. The present invention is even more advantageous in industrial applications comprising a process line including light-transmitting conduit sections in that control and monitoring of the process stream can be performed by simply installing the light-transmitting device 10 on the process line externally of a light-transmitting conduit section thereof, that is without having to replace a segment of the process line by a light-transmitting conduit section, thereby obviating any process interruption. That is to say that in those applications, the process line does not have to be modified in any way. One has only to mount the light-transmitting device 10 externally on a light-transmitting conduit section of the process line.

Figure 1:
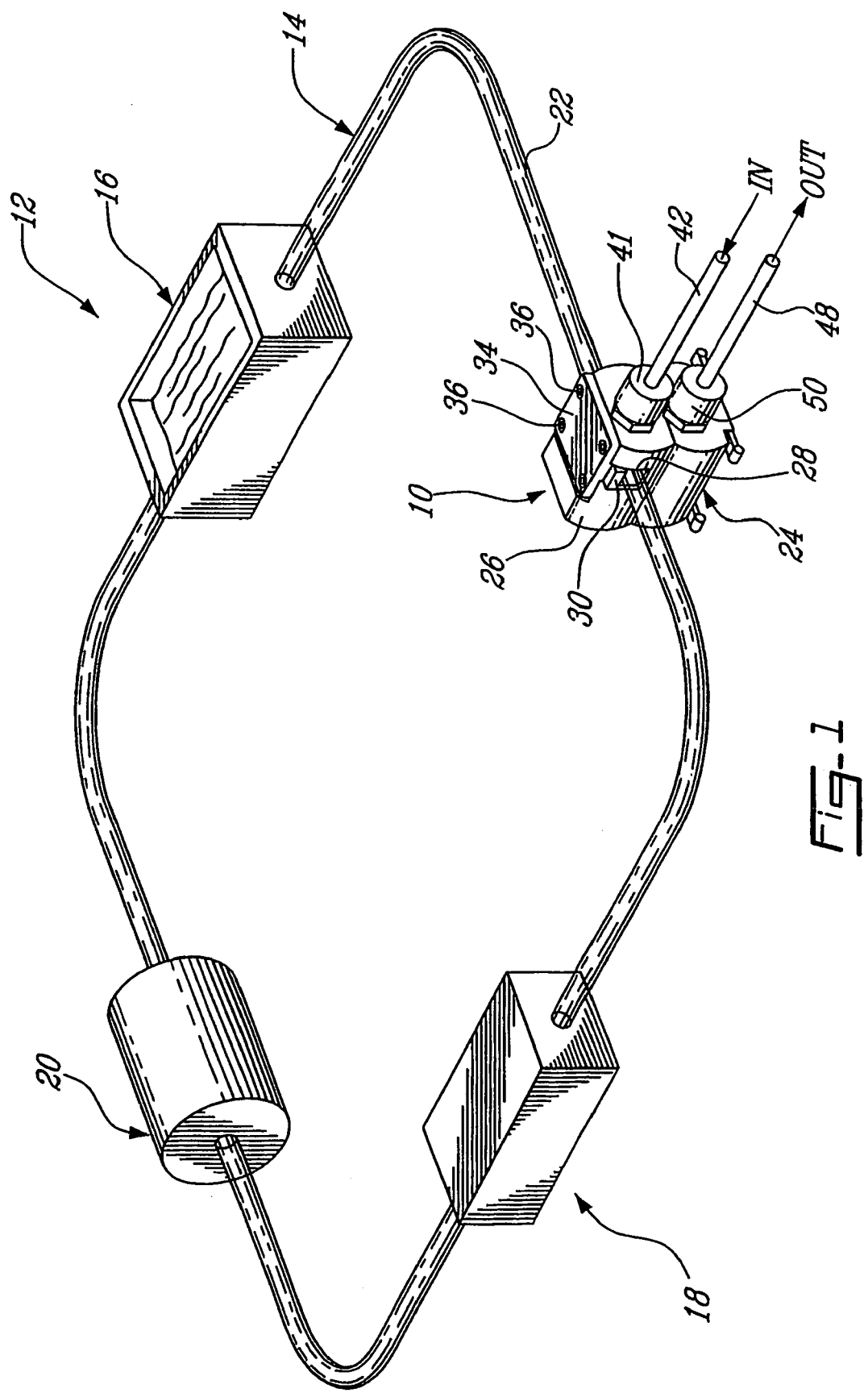
FIG. 1 is a schematic perspective view of a process line upon which a light-transmitting device in accordance with the present invention is externally mounted for allowing spectrum analysis of a process stream through the process line tubing.
Figure 2:
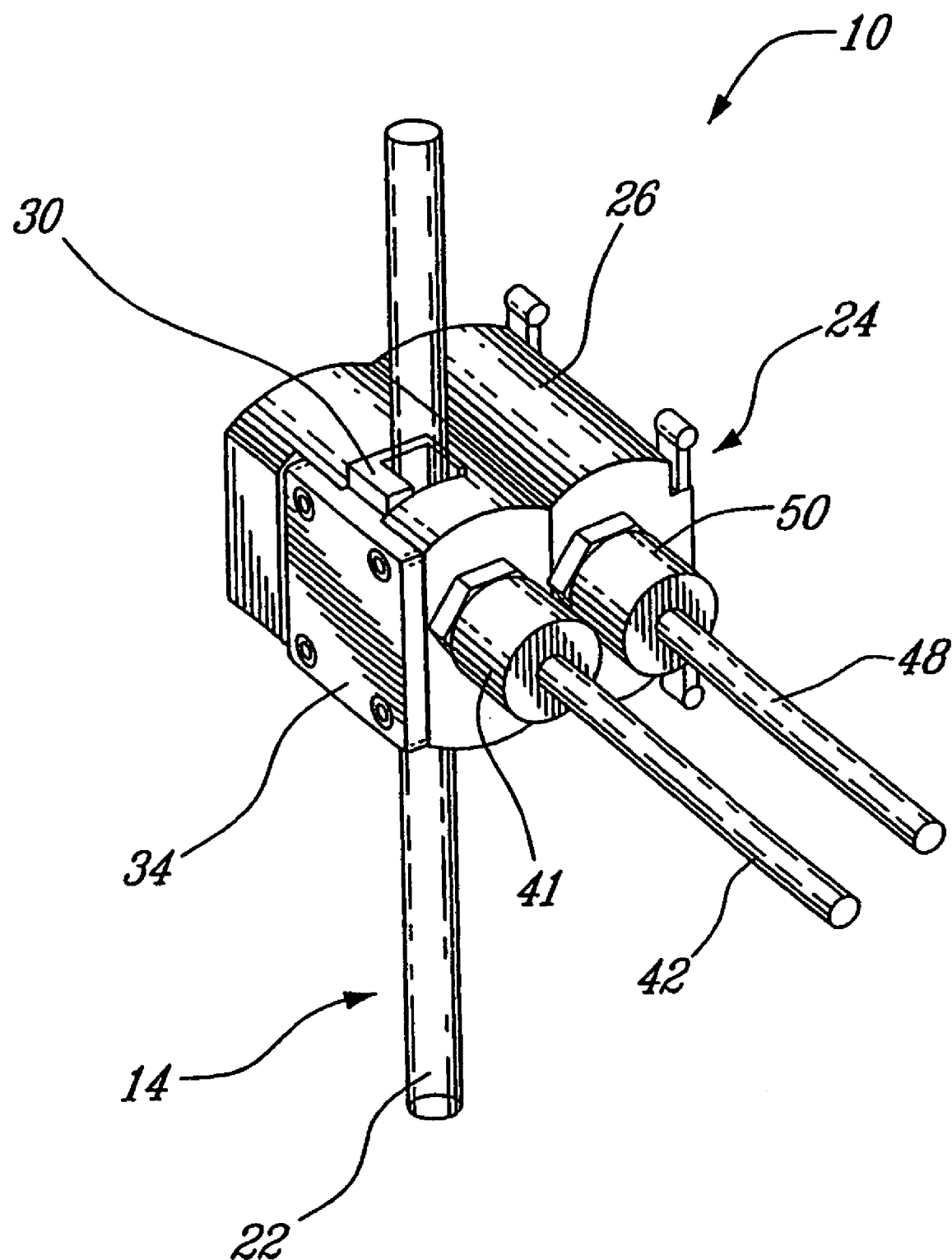
FIG. 2 is an enlarged view of the light-transmitting device mounted on a section of the process line.

FIG. 1 exemplifies one possible application of the present invention. More specifically, FIG. 1 depicts a wet station 12, such as those found in semiconductor industries. The wet station 12 essentially comprises a re-circulation line 14 composed of a bath 16, a filter 18, and a pump 20 connected together in a closed circuit via Teflon™ tubing 22. The bath 16 can contained various solutions, such as cleaning, stripping or etching solutions.

As seen in FIG. 1, the light-transmitting device 10 is directly installed on a selected conduit section of the existing process line 14 externally of the Teflon™ tubing 22. The light-transmitting device 10 generally comprises a clip 24 adapted to be detachably secured on a variety of conduits or tubes having different external diameters.

Figure 3:
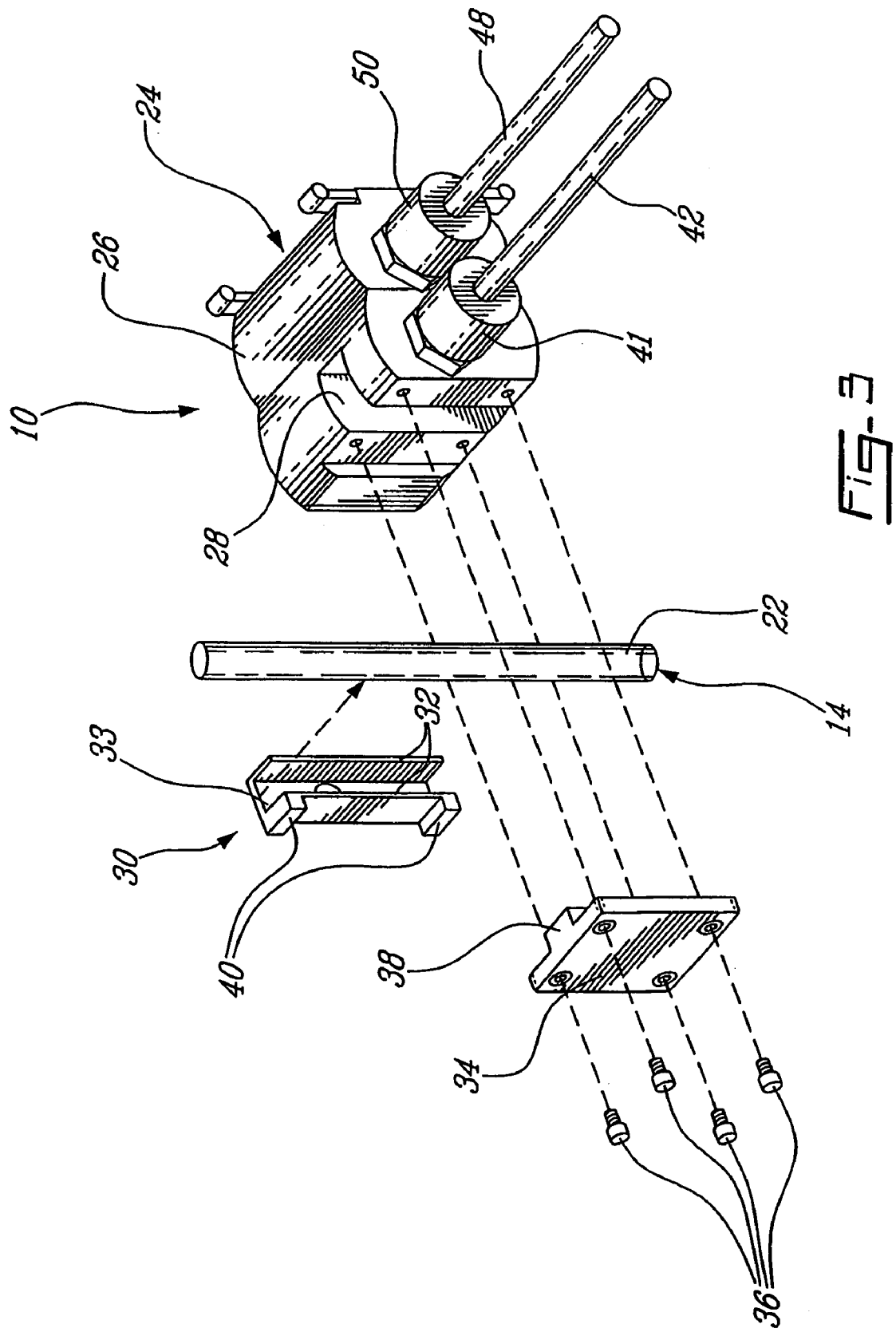
FIG. 3 is an enlarged partly exploded view of the light-transmitting device illustrating how the device is removably secured about a section of the process line.

The clip 24 has a hollow body 26 defining a peripheral open-ended elongated slot 28 adapted to receive one of a plurality of interchangeable conduit adapters, one of which is illustrated at 30 in FIG. 3. A different conduit adapter is used for each diameter of conduit, thereby allowing the body 26 to be mounted on a wide variety of conduits. The conduit adapter 30 includes a pair of spaced-apart conduit gripping arms 32 extending perpendicularly from a base wall 33 for tightly grasping a conduit or tube having an external diameter slightly greater than the spacing between the gripping arms 32. At least the base wall 33 of the adapter 30 is made of a light-transmitting material, such as but not limited to PTFE or other fluorinated hydrocarbon polymers. Once the right adapter has been chosen and fitted over the selected conduit section of the process line 14, the body 26 is brought over the adapter 30 to locate the same within the slot 28 in the body 26. The adapter 30 is retained captive in the slot 28 by a cover plate 34. The cover plate 34 is removably secured to the body 26 by means of screws 36. The cover plate 34 is provided on an undersurface thereof with an elongated locking rib 38 for engagement between a pair of axially spaced-apart locking fingers 40 extending laterally outwardly from one of the gripping arms 32 of the conduit adapter 30 to lock the latter against axial sliding movement in the slot 28.

Figure 4:
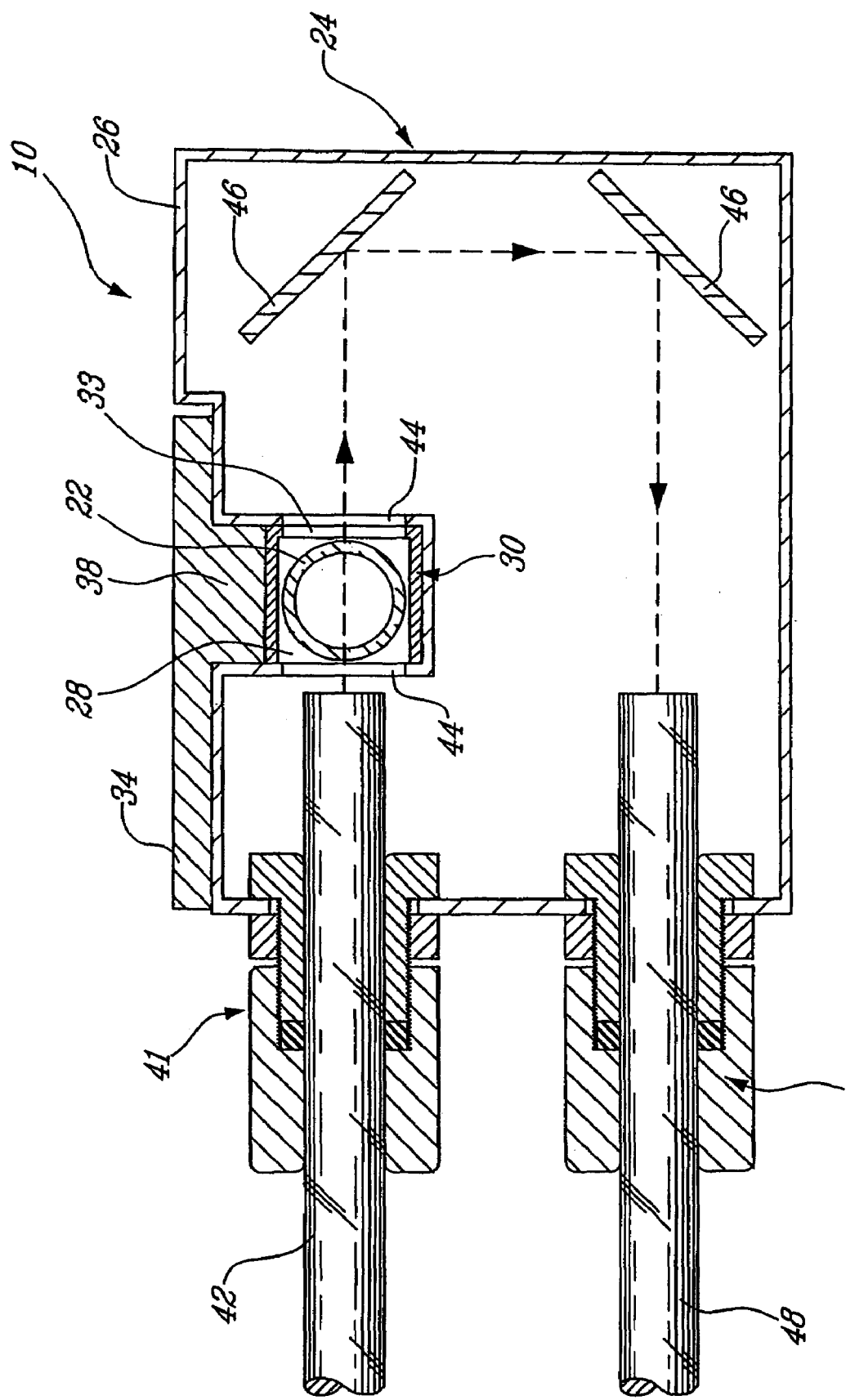
FIG. 4 is a cross-sectional view of the light-transmitting device mounted on the process line.

As shown in FIG. 4, the body 26 is provided on one side of the slot 28 thereof with a first connector 41 for receiving the distal end portion of a first fiber optic cable 42. The first fiber optic cable 42 is connected at an opposed proximal end thereof to a light source (not shown) for directing a light beam, such as but not limited to an infrared beam (IR beam) or a near infrared beam (NIR beam), transversally through the conduit section of the Teflon™ tubing 22 of the process line 14. The sidewalls of the slot 28 can be made of a light-transmitting material for allowing the light beam to pass therethrough or, alternatively a pair of opposed aligned light-transmitting windows 44 could be formed therein. The windows 44 could be provided in the form of holes. The light beam is directed so as to perpendicularly intersect the central axis of the conduit section on which the clip 24 is mounted.

According to the illustrated embodiment of the present invention, the light that emerges from the illuminated process solution through the conduit section of the Teflon™ tubing 22, the base wall 33 of the conduit adapter 30 and one of the sidewalls of the slot 28 is diverted 180 degrees by a pair of flat mirrors 46 (see FIG. 4) before being transmitted to a light receiving sensor via a second fiber optic cable 48 connected at a distal end portion thereof to the body 26 of the clip 24 by a second connector 50. According to one embodiment of the present invention, the flat mirrors 46 are mounted within the hollow body 26 of the clip 24 by means of an aluminum frame (not shown). It is noted that a lens could also be provided to focus the transmitted light into the second fiber optic cable 48 or, alternatively, directly into the light receiving sensor. Furthermore, it is noted that the second connector 50 could be disposed on a side of the slot 28 opposite the first connector and in alignment therewith. In fact, a variety of optical elements could be integrated within the hollow body 26 of the clip 24 to cause the light to follow various optical paths between the light source and the light-receiving sensor.

According to an embodiment of the present invention, the hollow body 26 of the clip 24 is made of Teflon™ to protect the optical elements housed therein from a corrosive surrounding environment. However, it is understood that the clip 24 could be made out of a wide variety of materials.

In the case of a tubing 22 made of non optically transparent or translucent material, a section of such tubing could be replaced once by an appropriate conduit section, and then the light-transmitting device 10 could be used, when required, thereon, i.e. without further changes to the tubing of the process line.

As can be appreciated from the foregoing, the present invention allows for on-line spectrum measurement for determining the chemical composition and/or properties of a substance through an existing conduit section in which the substance is circulated.

It is easily seen that the present invention as described above has many advantages that can be summarized as follows: no sample preparation, rapid installation with no process interruption, totally non-contact, non-intrusive for no possibility of contamination, etc.

The invention claimed is:

1. A non-intrusive device for allowing spectrum analysis of a confined process stream through a process line, comprising a light-transmitting conduit section having a circular wall defining a closed section through which the process stream flows, a clip adapted to be externally mounted on the light-transmitting conduit section, said clip being at least partly made of a light-transmitting material, an input fiber optic cable connectable to said clip and having a light delivery end disposed outside of the conduit section on a first side thereof for directing a beam of light from a source of light though the circular wall of the conduit section and transversally through the process stream flowing through the conduit section, the light delivery end of the input fiber optic cable being separated from the process stream by the circular wall of the conduit section, an output fiber optic cable connectable to said clip and having a receiving end disposed outside of the conduit section for transmitting light emanating from the circular wall of the conduit section to a light-receiving sensor, and wherein said clip includes a hollow body housing at least one optical element, the optical element focussing the light emanating from the input fiber optic cable into the output fiber optic cable transversely through the process stream and the circular wall of the light-transmitting conduit section, the optical element being disposed remotely outside of the light-transmitting conduit section,. the circular wall of the conduit section preventing the process stream from contacting the optical element, the input and output fiber optic cables.

2. A non-intrusive device as defined in claim 1, wherein said clip is adapted to be releasably secured about the light-transmitting conduit section.

3. A non-intrusive device as defined in claim 1, wherein said clip is adjustable so as to be securable on light-transmitting conduits having different cross-sectional dimensions.

4. A non-intrusive device as defined in claim 1, wherein said body defines a peripheral slot for receiving interchangeable conduit adapters adapted to grip conduits of different external diameters.

5. A non-intrusive device as defined in claim 4, wherein said clip further includes a removable cover for maintaining a selected one of said interchangeable conduit adapters captive in said peripheral slot.

6. A non-intrusive device as defined in claim 1, wherein said body defines a peripheral slot having walls made of a light-transmitting material.

7. A non-intrusive device as defined in claim 6, wherein said body has a first connector adapted to be connected to the input fiber optic cable to direct the beam of light through said peripheral slot and though the light-transmitting conduit section on which the clip is mounted, and wherein said at least one optical element comprises a lens.

8. A non-intrusive device as defined in claim 7, wherein said body has a second connector adapted to be connected to a light-receiving sensor for receiving the light emanating from the process stream through the light-transmitting conduit and the peripheral slot of the clip.

9. A non-intrusive device as defined in claim 8, wherein said second connector is connectable to said light-receiving sensor via the output fiber optic cable.

10. A non-intrusive device as defined in claim 1, wherein said body has a peripheral slot defining an optical path therethrough for receiving and conducting the beam of light through the light-transmitting conduit section of the process line, said at least one optical element collecting the light transmitted through the conduit section.

11. A non-intrusive device as defined in claim 10, wherein a conduit adapter is removably installed in said slot, said conduit adapter having a base wall from which extends a pair of spaced-apart conduit gripping arms adapted to receive therebetween the light-transmitting conduit section, wherein said conduit adapter is at least partly made of a light-transmitting material.

12. A conduit-mounted light-transmitting device in combination with a light-transmitting conduit section mounted in a process line for allowing optical analysis of a substance in the process line, the light-transmitting conduit section having a tubular light-transmitting wall defining an inner passage for conveying the substance, the conduit-mounted light-transmitting device comprising a clip detachably securable about the conduit section, said clip defining an optical path extending through said tubular light-transmitting wall and said inner passage when said clip is secured about the conduit section, wherein said clip has a substantially hollow body having a conduit engaging section by which said body is releasably mounted directly on the light-transmitting conduit section, said optical path extending through said conduit engaging section for receiving and conducting a beam of light through the light-transmitting conduit section, and at least one optical element housed within said body for collecting the light transmitted through the conduit section, said optical element focussing the transmitted light transmitted through the tubular light-transmitting wall of the conduit section into an output fiber optic cable removably coupled to the clip via a connector provided on said body, the optical element being disposed externally of the light transmitting conduit section between an outer surface of the light transmitting conduit section and the output fiber optic cable.

13. A combination as defined in claim 12, wherein said conduit engaging section includes an open ended slot defined in one face of the body, and a conduit adapter removably installed in said open ended slot, said conduit adapter having a base wall from which extends a pair of spaced-apart conduit gripping arms for receiving therebetween the light-transmitting conduit section, wherein said conduit adapter is at least partly made of a light-transmitting material.

14. A combination as defined on claim 12, wherein said body has a first connector adapted to be connected to an input fiber optic cable to direct a beam of light through said conduit engaging section and through the light-transmitting conduit section on which the clip is mounted.

15. A combination as defined in claim 12, wherein light-transmitting material is selected from a group consisting of: near infrared transmitting material and infrared transmitting material.

16. A combination as defined in claim 14, wherein said clip includes a body having a conduit-engaging section, said conduit engaging section being made of a light-transmitting material.

* * * * *